United States Patent
Steckel et al.

(10) Patent No.: US 9,731,021 B2
(45) Date of Patent: Aug. 15, 2017

(54) HYDROGEL COMPOSITION FOR THE TREATMENT OF DERMATOLOGICAL DISORDERS

(71) Applicant: Intendis GmbH, Berlin (DE)

(72) Inventors: Hartwig Steckel, Schonkirchen (DE); Karin Hoffmann, Berlin (DE)

(73) Assignee: INTENDIS GMBH, Berlin (DE)

( * ) Notice: Subject to any disclaimer, the term of this patent is extended or adjusted under 35 U.S.C. 154(b) by 117 days.

(21) Appl. No.: 14/541,784

(22) Filed: Nov. 14, 2014

(65) Prior Publication Data

US 2015/0182630 A1    Jul. 2, 2015

Related U.S. Application Data

(63) Continuation of application No. 12/644,494, filed on Dec. 22, 2009, now abandoned.

(60) Provisional application No. 61/140,107, filed on Dec. 23, 2008.

(30) Foreign Application Priority Data

Dec. 23, 2008 (EP) .................................. 08075966

(51) Int. Cl.
| | | |
|---|---|---|
| *A61K 47/14* | (2017.01) | |
| *A61K 47/24* | (2006.01) | |
| *A61K 47/38* | (2006.01) | |
| *A61K 8/04* | (2006.01) | |
| *A61K 8/34* | (2006.01) | |
| *A61K 8/55* | (2006.01) | |
| *A61K 8/81* | (2006.01) | |
| *A61K 9/06* | (2006.01) | |
| *A61K 47/10* | (2017.01) | |
| *A61Q 19/00* | (2006.01) | |
| *A61K 47/12* | (2006.01) | |
| *A61K 9/00* | (2006.01) | |

(52) U.S. Cl.
CPC .............. *A61K 47/38* (2013.01); *A61K 8/042* (2013.01); *A61K 8/345* (2013.01); *A61K 8/553* (2013.01); *A61K 8/8147* (2013.01); *A61K 9/06* (2013.01); *A61K 47/10* (2013.01); *A61K 47/12* (2013.01); *A61K 47/14* (2013.01); *A61K 47/24* (2013.01); *A61Q 19/00* (2013.01); *A61K 9/0014* (2013.01)

(58) Field of Classification Search
None
See application file for complete search history.

(56) References Cited

U.S. PATENT DOCUMENTS

| | | | |
|---|---|---|---|
| 5,888,540 A | 3/1999 | Sugden et al. | |
| 5,955,109 A | 9/1999 | Won et al. | |
| 6,211,296 B1 * | 4/2001 | Frate | A61K 9/7023 524/517 |
| 6,534,070 B1 | 3/2003 | Franke et al. | |
| 2003/0119783 A1 | 6/2003 | Chang et al. | |
| 2005/0026982 A1 | 2/2005 | Johannsen et al. | |

FOREIGN PATENT DOCUMENTS

| | | | |
|---|---|---|---|
| EP | 1 588 697 A1 | 10/2005 | |
| WO | WO 99/25332 A1 | 5/1999 | |
| WO | WO 9925332 A1 * | 5/1999 | ........... A61K 9/0014 |
| WO | WO 2006/062740 A2 | 6/2006 | |
| WO | WO 2007/082780 A1 | 7/2007 | |

OTHER PUBLICATIONS

Hoffman, Hydrogels for biomedical applications, Ann N Y Acad Sci. Nov. 2001; 944:62-73.*
Versenetm Na Disodium EDTA Chelating Agent, Oct. 2009, available at http://msdssearch.dow.com/PublishedLiteratureDOWCOM/dh_0421/0901b80380421c33.pdf?filepath=versene/pdfs/noreg/113-01340.pdf&fromPage=GetDoc.*
Partial European Search Report of EP 08 07 5966 (May 28, 2009).
Z. H. Hafeez, "Perioral Dermatitis: An Update", International Journal of Dermatology, vol. 42, No. 7 (2003) pp. 514-517.
U. R. Hengge et al., "Adverse Effects of Topical Glucocorticosteroids", Journal of American Academy of Dermatology, vol. 54, No. 1 (2006) pp. 1-15.
Versene™ NA Disodium EDTA Chelating , Oct. 2009 downloaded at http://msdssearch.dow.com/PublishedLiteratureDOWCOM/dh_0421/0901b80380421c33.pdf?filepath=versene/pdfs/noreg/113-01340.pdf&fromPage=GetDoc.
Hoffman, Hydrogels for biomedical applications , Ann NY Acad. Sci Nov. 2001 944:62-73.

* cited by examiner

*Primary Examiner* — Svetlana M Ivanova
(74) *Attorney, Agent, or Firm* — McBee Moore Woodward Vanik IP; Susan McBee; David Woodward

(57) ABSTRACT

The present patent application is related to a hydrogel composition which is essentially free of active drugs for the manufacture of a product for the treatment of dermatological disorders, especially perioral dermatitis, acne or seborrheic dermatitis.

5 Claims, 3 Drawing Sheets

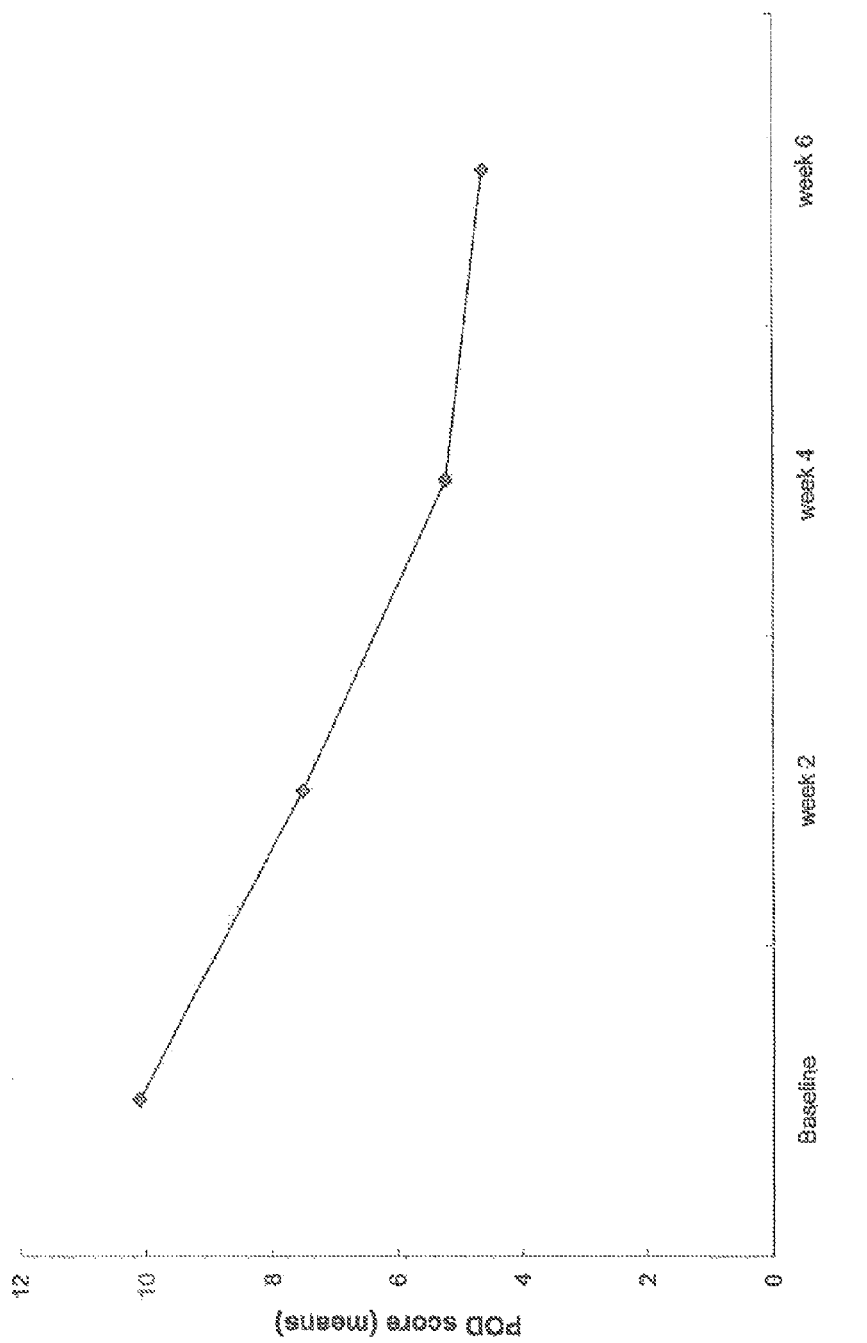

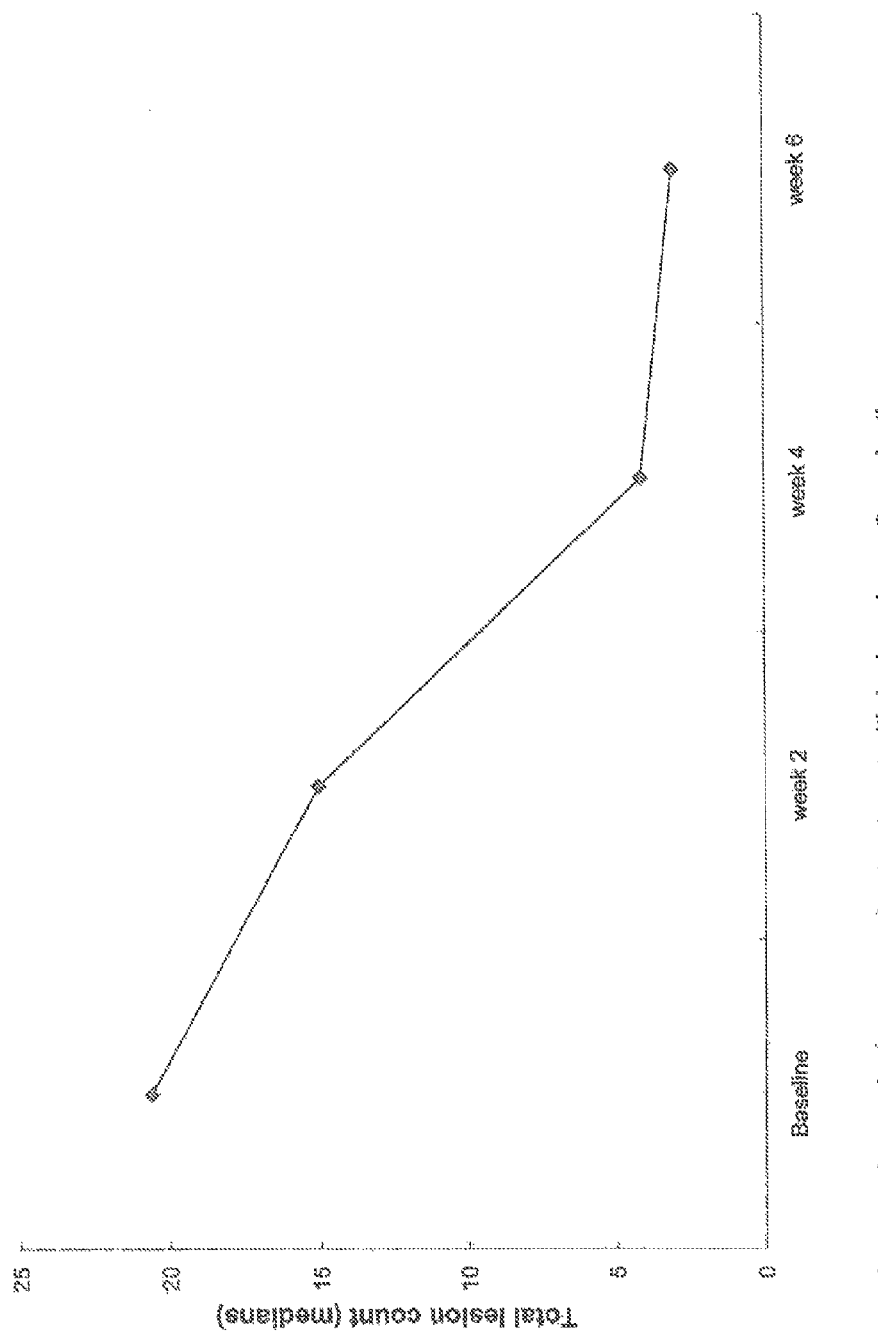

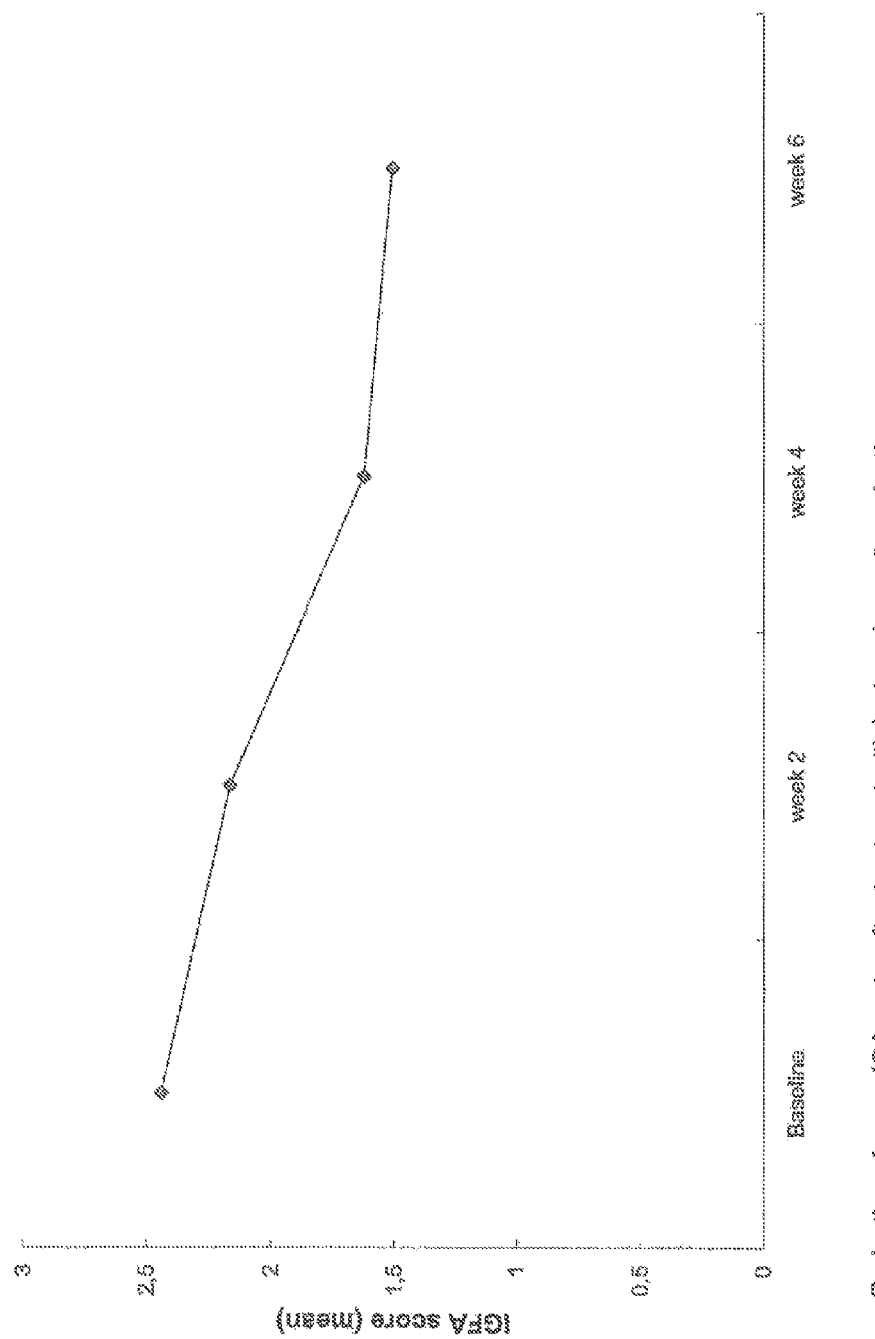

HYDROGEL COMPOSITION FOR THE TREATMENT OF DERMATOLOGICAL DISORDERS

This application is a continuation of Ser. No. 12/644,494 filed Dec. 22, 2009 which claims the priority according to the Paris Convention of the European Patent application EP 08075966.5 (filing date: Dec. 23, 2008) as well as all benefits from earlier U.S. application Ser. No. 61/140,107 (filing date: Dec. 23, 2008), which are both incorporated herein by reference.

BACKGROUND OF THE INVENTION

Perioral dermatitis is a dermatological disorder of unclear origin. The patients suffer from red papules that typically effects the perioral area, nasolbial folds or perioccular area (Hafeez: Int J. Dermatol. 2003, 42(7):514) sometimes accompanied by mild peeling. Itching or burning are reported from patients. Females are more likely to be affected.

A number of treatments have been suggested including oral antibiotics (e.g. tetracycline), topical antibiotics (such as metronidazole), immunomodulating agents (such as Pimecrolimus) and corticosteroids (such as mometasone furoate). However, these treatments have been criticised for their side-effects (Hengge: J Am Acad Dermatol. 2006, 54(1): 1-15).

Perioral dermatitis may also be treated following the "Null" therapy, i.e. to do anything about the dermatitis and wait until improvement. This "Null" therapy is often not acceptable from a patient's perspective as the signs of the perioral dermatitis are cosmetically in-elegant and might affect the patients mind.

Hydrogels are commonly known as a carrier for active drug substances for the topical delivery of drugs for the treatment of e.g. acne, rosacea, burns or pruritus. As such, hydrogels offer a cooling effect to the skin, thereby supporting the therapeutic action of the incorporated active drug substance.

Examples of such hydrogel formulations including an active drug substance are, for instance, disclosed in US 2003/119783 describing an aqueous vehicle containing metronidazole in a gel for the treatment of rosacea.

U.S. Pat. No. 5,955,109 describes an aqueous gelated vehicle containing the active drug substance tretinoin bound to polymer particles for the treatment of acne.

Further embodiments of hydrogels are provided in WO 99/25332, US 2005/026982, WO 2007/082780. However, all of these formulations contain at least one active drug substance (pharmaceutically active ingredient) which are not in the scope of the present invention.

Surprisingly, we have now found that a hydrogel composition as described within this application which does not contain any active drug substance is useful in treating dermatological disorders, especially perioral dermatitis.

The object of the present invention is therefore the use of a hydrogel composition which is essentially free of active drug compounds for the manufacture of a product for the treatment of perioral dermatitis.

The term "active drug compound" or "pharmaceutically active ingredient" refers to compounds with proved pharmaceutical activity demonstrated in clinical trials and approved as a drug by the European Medicines Agency (EMEA) or the US Food and Drug Administration (FDA). The term "essentially free of active drug compound" or "essentially free of pharmaceutically active ingredients" means that no "active drug compound" or "pharmaceutically active ingredient" has been intended to be added to the composition. The total amount of pharmaceutically active ingredients as a result of unintended contamination is therefore well below 0.05%, preferably below 0.01%. Most preferred is a composition in which no amount of any active drug compound (pharmaceutical ingredient) can be detected with standard analytical methods used in pharmaceutical technology.

The hydrogel composition according to the invention is preferably based on a mixture of propylene glycol, polyacrylic acid, medium-chain triglycerides and lecithine as described in the examples section. Various further ingredients may be added. Benzoic acid is preferably added as a preservative. It is important to know that benzoic acid alone applied in the amounts described below does not provide any effect in the treatment of perioral dermatitis or other dermatological disorder. Benzoic acid is therefore not considered to be an active drug compound according to this invention.

A composition in form of a hydrogel which is essentially free of active pharmaceuticals is therefore an object of the invention. More specifically an object of the invention is a composition in form of a hydrogel which is essentially free of active pharmaceuticals, wherein the hydrogel contains at least a surfactant, propylene glycol, lecithin and a lipid. A preferred embodiment of the invention is a composition in form of a hydrogel which is essentially free of active pharmaceuticals according to claim 1, wherein the hydrogel contains (i) 5-15% propylene glycol
(ii) 0-2% polyacrylic acid
(iii) 0.5-3% lecithin
(iv) 0.5-3% medium chain triglycerides or macrogol-glycerol hydroxystearate.

The most preferred embodiments of the invention are provided in Example 1.

The hydrogel is manufactured according to prior art methods, such as in U.S. Pat. No. 6,534,070.

Surprisingly, the composition according to the invention does show (in addition to its effect in perioral dermatitis as described herein) beneficial effects in the treatment of various kinds of dermatological disorders, such as acne (e.g. Acne vulgaris) and seborrheic dermatitis.

It is therefore a further object of the invention to provide a method of treatment for humans suffering from dermatological disorders, such as perioral dermatitis, seborrhoic dermatitis or acne, by topical administration of a hydrogel as described in this document.

BRIEF DESCRIPTION OF THE DRAWINGS

FIG. 1 shows the reduction of mean perioral dermatitis (POD) score after treatment with hydrogel over 6 weeks time.

FIG. 2 shows the reduction of mean lesion count after treatment with hydrogel over 6 weeks time.

FIG. 3 shows the reduction of mean IGA score after treatment with hydrogel over 6 weeks time.

EXAMPLES

1.) Examples for hydrogels to be used in the indication perioral dermatitis or in the indication, seborrhoic dermatitis':

|  | 1 | 2 | 3 | 4 | 5 | 6 | 7 | 8 | 9 |
|---|---|---|---|---|---|---|---|---|---|
| Benzoic acid | 0.1 | 0.1 | 0.1 | 0.1 | 0.1 | 0.1 | 0.1 | 0.1 | 0.1 |
| Sodium edetate | 0.1 | 0.1 | 0.1 | 0.1 | 0.1 | 0.1 | 0.1 | 0.1 | 0.1 |
| Sodium hydroxide | 0.2 | 0.1 | 0.2 | 2 | — | 0.1 | 0.1 | 0.2 | 0.2 |
| Polyacrylic acid | 1.0 | — | 1.0 | 1.0 | — | 0.5 | — | 1.0 | — |
| Acrylic acid copolymer | — | 0.5 | — | — | — | — | 0.3 | — | — |
| Hydroxyethylcellulose | — | — | — | — | — | — | — | — | 0.5 |
| Xanthan gum | — | — | — | — | 0.8 | 0.5 | 0.3 | — | — |
| Propylene glycol | 12.0 | 8.0 | 12.0 | 6.0 | 12.0 | 12.0 | 12.0 | 8.0 | 8.0 |
| Glycerol | — | — | — | 6.0 | — | — | — | 8.0 | — |
| Polysorbate 80 | 1.5 | 1.5 | 1.5 | — | 1.5 | 1.5 | 1.5 | 1.5 | 1.5 |
| Macrogol-glycerol-hydroxystearate | — | — | — | 1.5 | — | — | — | — | — |
| Medium chain triglycerides | 1.0 | 2.0 | 1.0 | 1.0 | 1.0 | 3.0 | 3.0 | 1.0 | 1.0 |
| Dimeticone | — | — | 1.0 | — | — | — | — | — | — |
| Liquid paraffin | — | — | — | — | 1.0 | — | — | — | — |
| Lecithin | 1.0 | 2.0 | 1.0 | 1.0 | 1.0 | 1.5 | 1.0 | 1.0 | 1.0 |
| Purified water to | 100.0 | 100.0 | 100.0 | 100.0 | 100.0 | 100.0 | 100.0 | 100.0 | 100.0 |

Data provided in weight percent (wt. %).

2) In a recent observational study, 16 patients suffering from perioral dermatitis were treated with an active-free (=free of any active pharmaceutical ingredient) hydrogel formulation. Surprisingly, we observed a significant improvement of overall lesion count, perioral dermatitis (POD) score and investigators global assessment (IGA) score (FIG. 1-3).

3.) Patients suffering from Acne vulgaris are treated twice daily with one of the compositions according to Example 1. Surprisingly after 6 weeks the majority of the patients show a clinically remarkably improvement of their skin disorder.

4.) Patients suffering from seborrheic dermatitis are treated twice daily with one of the compositions according to Example 1. Surprisingly after 6 weeks the majority of the patients show a clinically remarkably improvement of their dermatological disease.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding European application No. 08075966.5, filed Dec. 23, 2008, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A composition in form of a hydrogel which contains less than 0.01% of active pharmaceuticals, wherein the hydrogel contains
   (i) 5-15% propylene glycol
   (ii) 0-2% polyacrylic acid
   (iii) 0.5-3% lecithin
   (iv) 0.5-3% medium chain triglycerides or macrogol-glycerol hydroxystearate.

2. The composition in form of a hydrogel which contains less than 0.01% of active pharmaceuticals according to claim 1, wherein the hydrogel consists of one of the following compositions:

|  | 1 | 2 | 3 | 4 | 5 | 6 | 7 | 8 | 9 |
|---|---|---|---|---|---|---|---|---|---|
| Benzoic acid | 0.1 | 0.1 | 0.1 | 0.1 | 0.1 | 0.1 | 0.1 | 0.1 | 0.1 |
| Sodium edetate | 0.1 | 0.1 | 0.1 | 0.1 | 0.1 | 0.1 | 0.1 | 0.1 | 0.1 |
| Sodium hydroxide | 0.2 | 0.1 | 0.2 | 2 | — | 0.1 | 0.1 | 0.2 | 0.2 |
| Polyacrylic acid | 1.0 | — | 1.0 | 1.0 | — | 0.5 | — | 1.0 | — |
| Acrylic acid copolymer | — | 0.5 | — | — | — | — | 0.3 | — | — |
| Hydroxyethylcellulose | — | — | — | — | — | — | — | — | 0.5 |
| Xanthan gum | — | — | — | — | 0.8 | 0.5 | 0.3 | — | — |
| Propylene glycol | 12.0 | 8.0 | 12.0 | 6.0 | 12.0 | 12.0 | 12.0 | 8.0 | 8.0 |
| Glycerol | — | — | — | 6.0 | — | — | — | 8.0 | — |
| Polysorbate 80 | 1.5 | 1.5 | 1.5 | — | 1.5 | 1.5 | 1.5 | 1.5 | 1.5 |
| Macrogol-glycerol-hydroxystearate | — | — | — | 1.5 | — | — | — | — | — |
| Medium chain triglycerides | 1.0 | 2.0 | 1.0 | 1.0 | 1.0 | 3.0 | 3.0 | 1.0 | 1.0 |
| Dimeticone | — | — | 1.0 | — | — | — | — | — | — |
| Liquid paraffin | — | — | — | — | 1.0 | — | — | — | — |
| Lecithin | 1.0 | 2.0 | 1.0 | 1.0 | 1.0 | 1.5 | 1.0 | 1.0 | 1.0 |
| Purified water to | 100.0 | 100.0 | 100.0 | 100.0 | 100.0 | 100.0 | 100.0 | 100.0 | 100.0. |

3. A method for the treatment of perioral dermatitis, acne or seborrheic dermatitis, comprising administering a hydrogel which contains less than 0.01% of active pharmaceuticals, wherein the hydrogel contains
   (i) 5-15% propylene glycol
   (ii) 0-2% polyacrylic acid
   (iii) 0.5-3% lecithin
   (iv) 0.5-3% medium chain triglycerides or macrogol-glycerol hydroxystearate.

4. The method for the treatment of perioral dermatitis, acne or seborrheic dermatitis according to claim 3, wherein the hydrogel consists of one of the following compositions:

|  | 1 | 2 | 3 | 4 | 5 | 6 | 7 | 8 | 9 |
|---|---|---|---|---|---|---|---|---|---|
| Benzoic acid | 0.1 | 0.1 | 0.1 | 0.1 | 0.1 | 0.1 | 0.1 | 0.1 | 0.1 |
| Sodium edetate | 0.1 | 0.1 | 0.1 | 0.1 | 0.1 | 0.1 | 0.1 | 0.1 | 0.1 |
| Sodium hydroxide | 0.2 | 0.1 | 0.2 | 2 | — | 0.1 | 0.1 | 0.2 | 0.2 |
| Polyacrylic acid | 1.0 | — | 1.0 | 1.0 | — | 0.5 | — | 1.0 | — |
| Acrylic acid copolymer | — | 0.5 | — | — | — | — | 0.3 | — | — |
| Hydroxyethylcellulose | — | — | — | — | — | — | — | — | 0.5 |
| Xanthan gum | — | — | — | — | 0.8 | 0.5 | 0.3 | — | — |
| Propylene glycol | 12.0 | 8.0 | 12.0 | 6.0 | 12.0 | 12.0 | 12.0 | 8.0 | 8.0 |
| Glycerol | — | — | — | 6.0 | — | — | — | 8.0 | — |
| Polysorbate 80 | 1.5 | 1.5 | 1.5 | — | 1.5 | 1.5 | 1.5 | 1.5 | 1.5 |
| Macrogol-glycerol-hydroxystearate | — | — | — | 1.5 | — | — | — | — | — |
| Medium chain triglycerides | 1.0 | 2.0 | 1.0 | 1.0 | 1.0 | 3.0 | 3.0 | 1.0 | 1.0 |
| Dimeticone | — | — | 1.0 | — | — | — | — | — | — |
| Liquid paraffin | — | — | — | — | 1.0 | — | — | — | — |
| Lecithin | 1.0 | 2.0 | 1.0 | 1.0 | 1.0 | 1.5 | 1.0 | 1.0 | 1.0 |
| Purified water to | 100.0 | 100.0 | 100.0 | 100.0 | 100.0 | 100.0 | 100.0 | 100.0 | 100.0. |

5. A method of treatment of perioral dermatitis, acne or seborrheic dermatitis in a human, comprising topical administration of a hydrogel composition according to claim 1.

* * * * *